United States Patent [19]
Zweymüller et al.

[11] Patent Number: 5,456,717
[45] Date of Patent: Oct. 10, 1995

[54] STEM FOR A FEMORAL HIP-JOINT ENDOPROSTHESIS

[75] Inventors: K. Zweymüller, Vienna, Austria; André Deckner, Paris, France

[73] Assignee: Plus Endoprothtik AG, Switzerland

[21] Appl. No.: 164,731

[22] Filed: Dec. 7, 1993

[30] Foreign Application Priority Data

Dec. 7, 1992 [EP] European Pat. Off. .............. 92120835

[51] Int. Cl.⁶ ..................................................... A61F 2/12
[52] U.S. Cl. ................................................................ 623/8
[58] Field of Search .................. 623/16, 18, 22, 623/33

[56] References Cited

U.S. PATENT DOCUMENTS

| | | | |
|---|---|---|---|
| 4,642,121 | 2/1987 | Keller | 623/18 |
| 4,659,067 | 4/1987 | Fournier | 623/23 |
| 4,813,962 | 3/1989 | Deckner et al. | 623/23 |
| 4,865,608 | 9/1989 | Brooker, Jr. | 623/23 |
| 4,904,269 | 2/1990 | Elloy et al. | 623/23 |
| 4,908,035 | 3/1990 | Deckner et al. | 623/23 |
| 4,919,670 | 4/1990 | Dale et al. | 623/22 |
| 4,919,673 | 4/1990 | Willbert et al. | 623/23 |
| 4,919,679 | 4/1990 | Averill et al. | 623/23 |
| 4,936,863 | 6/1990 | Hofmann | 623/33 |
| 5,062,854 | 11/1991 | Noble et al. | 623/23 |
| 5,258,034 | 11/1993 | Furlong et al. | 623/23 |

FOREIGN PATENT DOCUMENTS

| | | |
|---|---|---|
| 0027159 | 4/1981 | European Pat. Off. .................. 623/23 |
| 0266081 | 10/1987 | European Pat. Off. . |
| 0363151 | 10/1989 | European Pat. Off. . |
| 2620623 | 3/1989 | France ..................................... 623/22 |
| 2633510 | 1/1990 | France ..................................... 623/22 |
| 2641462 | 7/1990 | France ..................................... 623/23 |
| 2652259 | 3/1991 | France ..................................... 623/23 |
| 9013271 | 11/1990 | WIPO . |

Primary Examiner—Randall L. Green
Attorney, Agent, or Firm—Andrus, Sceales, Starke & Sawall

[57] ABSTRACT

A stem for a femoral hip-joint endoprosthesis comprises a shaft which is substantially rectangular in cross section, with a distal and a proximal end. The distal end tapers substantially conically and the proximal end (16) comprises an insertion means and an extraction means for the insertion and for the extraction of the stem into a marrow space of a femur. A cone is provided to receive a joint ball, the cone being connected to the proximal end of the shaft by way of a neck. The insertion means and the extraction means at the proximal end of the shaft are positioned substantially on the median long axis of the stem so that force transmission during insertion and extraction is coaxial.

13 Claims, 3 Drawing Sheets

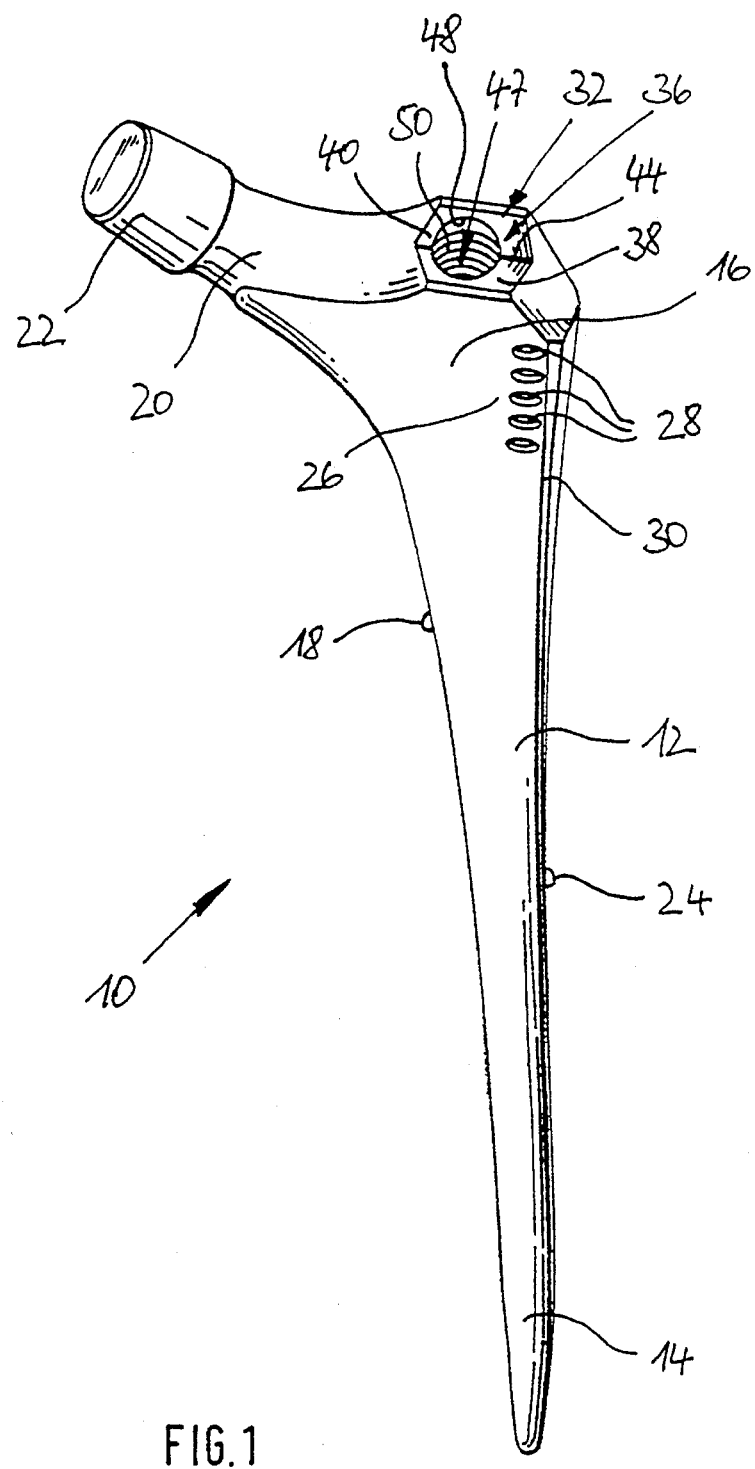
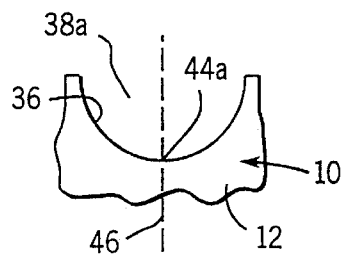
FIG. 3A
FIG. 1

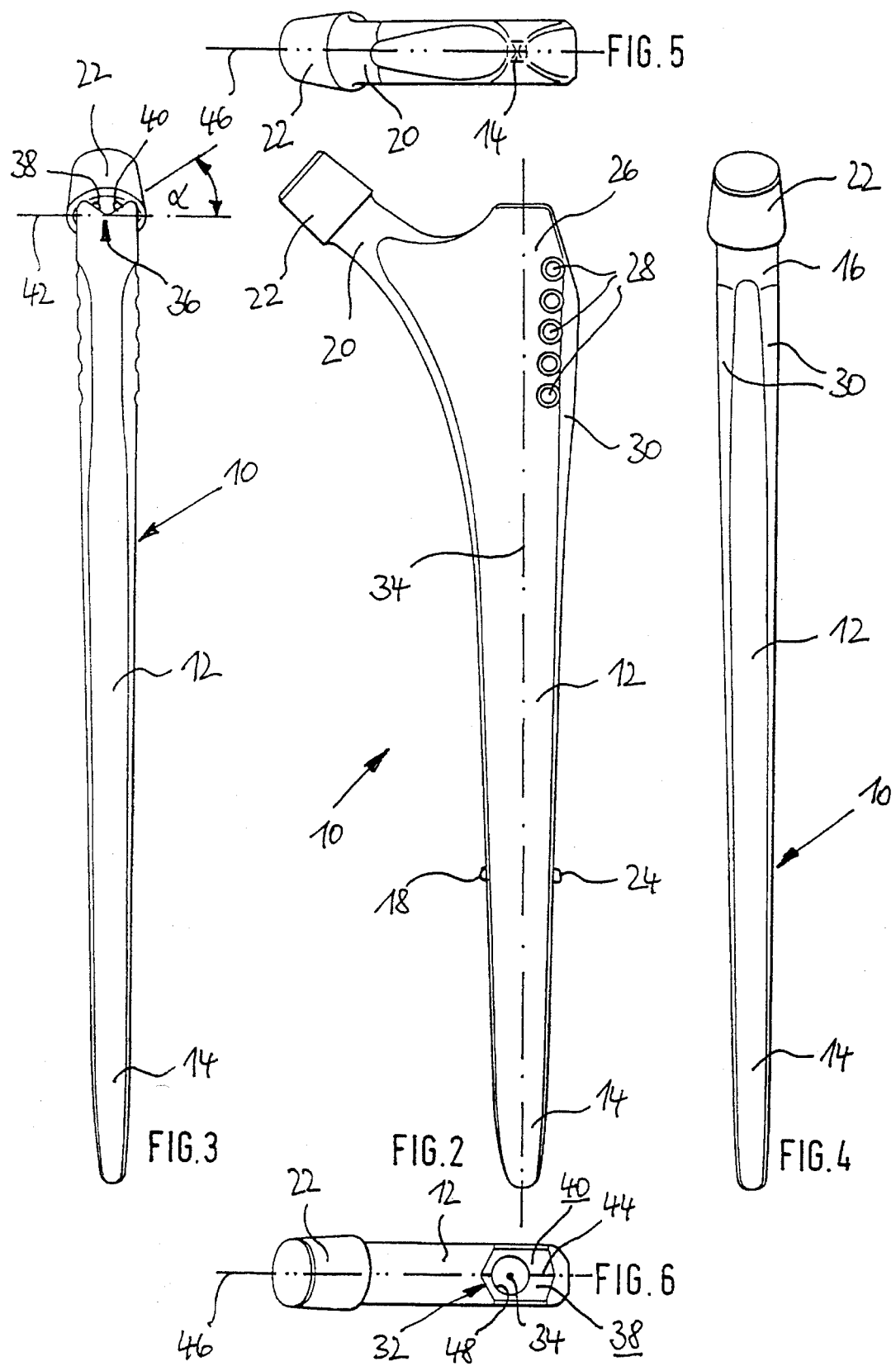

STEM FOR A FEMORAL HIP-JOINT ENDOPROSTHESIS

FIELD OF THE INVENTION

The present invention relates to a stem for a femoral hip-joint endoprosthesis.

DESCRIPTION OF THE PRIOR ART

A stem of this type for a femoral hip-joint endoprosthesis is described in European Patent B1-0244610. This stem comprises a shank approximately rectangular in cross section, with a distal and a proximal end. The distal end tapers essentially conically. The proximal end comprises a means for inserting the stem into the marrow cavity of the femur as well as a means for extracting the stem from the marrow cavity. The stem further comprises a cone joined by a neck to the proximal end of the shank, to receive a joint ball.

In practice this stem for a femoral hip-joint endoprosthesis has proved disadvantageous with respect to the means used for insertion and the means used for extraction of the stem. The insertion and extraction means comprise a bore in the proximal end of the stem, perpendicular to its median long axis and parallel to its median longitudinal plane. In order to insert the stem into the femur or to extract it from the femur, a substantially hook-shaped insertion and/or extraction tool is pushed into the bore from the side, starting from the cone mounted on the neck at the proximal end. Although such a construction is intended to avoid additional loss of bone in the trochanter region, when the stem is impacted into the marrow cavity of the femur the force acting laterally from the median long axis of the shank tends to tilt the stem, as a result of which the stem is relatively loosely seated in the marrow cavity. The consequence is that the service life of the hip-joint endoprosthesis as a whole is limited. Furthermore, when the stem is extracted from the marrow cavity of the femur force is again transmitted laterally from the median long axis of the shank, producing a tilting tendency that makes it considerably more difficult to withdraw the implant. Finally, during both insertion and extraction of the stem, due to the particular construction of the insertion and extraction means the special insertion and/or extraction tool has often been damaged by fracture.

SUMMARY OF THE INVENTION

The object of the present invention is to overcome or substantially mitigate the problems outlined above and to provide a stem for a femoral hip-joint endoprosthesis of this general kind in which force transmission during insertion and retraction is favorable so that as a result the stem is easy to position and remove and also has a high degree of stability and long life expectancy.

According to the present invention there is provided a stem for a femoral hip-joint endoprosthesis comprising a shaft of substantially rectangular cross section and defining a distal end and a proximal end, wherein the distal end tapers in a substantially conical manner; an insertion means located at the proximal end of the shaft for use in the insertion of the shaft into a marrow cavity of a femur; an extraction means located at the proximal end of the shaft for use in the extraction of the shaft from the marrow cavity of the femur; a cone to receive a joint ball, said cone being connected to the proximal end of the shaft; and a neck region forming the connection between said cone and said proximal end of the shaft; and wherein the improvement comprises the location of said insertion means and said extraction means at the proximal end of the shaft substantially on a median long axis of the stem so that force transmission during said insertion and said extraction of the stem is coaxial.

In this invention the insertion means and the extraction means are arranged at the proximal end of the shank, essentially on the median long axis of the shank, in such a way as to enable coaxial force transmission. Because of such an axial orientation of the insertion means, a precisely coaxial impact direction is achieved and tilting is avoided, so that the quality of the primary seating of the stem in accordance with the invention, and hence of the whole hip-joint endoprosthesis, is considerably improved. Because of such an axial orientation of the extraction means, again, a precisely coaxial extraction direction is achieved and tilting is avoided, so that manipulation during the surgical procedure is considerably simplified and repeated removal of the implant to fit the shank into the marrow cavity of the femur is possible without damaging the surrounding bone material. Finally, arrangement of the insertion means and extraction means on the median long axis of the shank in accordance with the invention results in very little wear and tear on the insertion and/or extraction tool.

Preferably, said insertion means comprises an abutment surface which extends substantially perpendicular to said median long axis of the stem and which provides an abutment for an insertion tool. This makes for a precise coaxial impact direction.

Preferably also, said abutment surface is of substantially V-shaped cross section pointing toward said distal end of the shaft.

In addition, the abutment surface preferably defines two faces forming said substantially V-shaped abutment surface, each of said faces defining an angle $\alpha$ in the range 15° to 45° inclusive with respect to a transverse plane perpendicular to a median longitudinal plane of the stem. Such construction of the abutment surface prevents, in a simple but at the same time very reliable manner, the insertion tool from sliding off the abutment surface of the insertion means at the proximal end of the shank.

Preferably also, said two faces of said substantially V-shaped abutment surface define a line of intersection which coincides with said median longitudinal plane of the stem. This feature ensures that the insertion tool placed on the abutment surface is centered with respect to the median longitudinal plane. As a result, force is transmitted precisely coaxially from the insertion tool to the stem itself. This in turn results in a high-quality primary seating of the stem and consequently of the whole hip-joint endoprosthesis.

Alternatively, said abutment surface is substantially concave and is recessed toward said distal end of the shaft. Preferably, said concave abutment surface defines an anticlinal line which coincides with a median longitudinal plane of the stem.

Preferably also, said insertion means defines a bore which is coaxial with said median long axis of the stem and which is capable of accepting a pin projecting from an insertion tool for centering and fixation of the tool.

Preferably also, said extraction means defines a bore with a screw thread for cooperation with an extraction tool, said bore being positioned so that the median long axis of the bore coincides with said median long axis of the stem. This threaded bore, which for example can cooperate with an extraction tool in the form of an extraction screw, allows extremely high extraction forces to be exerted on the stem in the marrow cavity of the femur, with no risk of damage to the extraction tool itself. In this way, for instance, the pulling action of the extraction tool on the extraction means is increased by at least a factor of 4 in comparison with the conventional stem. Furthermore, due to the special arrangement of the bore with respect to the median long axis of the stem, tilting forces are not generated as the stem is pulled out of the marrow cavity of the femur.

In order to simplify construction, the bore of the insertion means for the pin or the like projecting from the insertion tool is identical with the threaded bore of the extraction means for the extraction tool. In this case the first turn of the screw thread is set back within the bore so that the thread is not damaged during the insertion process.

Preferably also, the stem comprises a trochanter wing continuous with said proximal end of the shaft, and defining a lateral narrow surface which is adjacent to said trochanter wing and which leads to said distal end of the shaft, the lateral narrow surface bearing at least one longitudinal rib which is oriented substantially parallel to said median long axis of the stem in order to guide the stem during said insertion and said extraction.

Preferably also, said longitudinal rib is constructed by two components oriented to define a substantially V-shaped arrangement wherein they enclose an angle $\beta$ in a range of 90° to 120° inclusive. Preferably also, the stem is metallic and substantially of titanium, In particular, the stem is preferably substantially of the high-quality forged titanium alloy $Ti_6Al_7Nb$.

Preferably also, said shaft has an average surface roughness in the range of 3 to 5 µm inclusive. This is important for biological fixation by osteointegration of the femur with the shank itself.

Additional characteristics, advantages and details of the invention will become apparent in the following description of some preferred embodiments of the invention, with reference to the accompanying drawings

BRIEF DESCRIPTION OF THE DRAWINGS

FIG. 1 is a perspective side view of a first embodiment of a stem in accordance with the invention;

FIG. 2 is a side view of the stem shown in FIG. 1;

FIG. 3 is a back view of the stem shown in FIG. 1;

FIG. 3a is an end view similar to a portion of FIG. 3 illustrating an alternate construction of a force abutment surface.

FIG. 4 is a front view of the stem shown in FIG. 1;

FIG. 5 is a view from below of the stem shown in FIG. 1;

FIG. 6 is a view from above of the stem shown in FIG. 1; and

DESCRIPTION OF THE PREFERRED EMBODIMENTS

Figure 7:
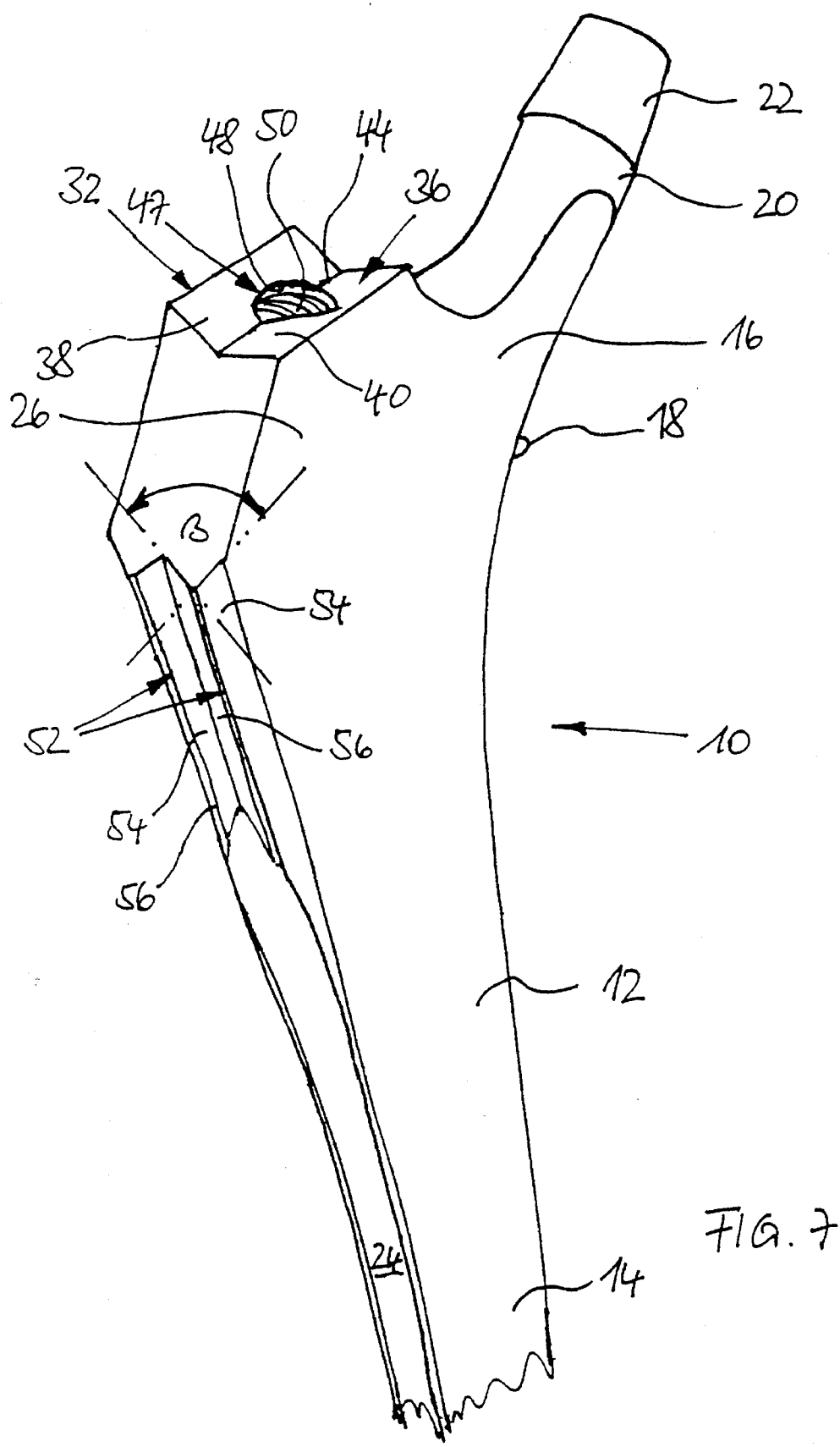
FIG. 7 is a partial perspective side view of a second embodiment of a stem in accordance with the invention, shown to a larger scale than the first embodiment in FIGS. 1 to 6.

The first embodiment of a stem 10 for a femoral hip-joint enoprosthesis shown in FIGS. 1 to 6 comprises a shank 12 which is of substantially rectangular cross section. The basically rectangular shape of the shank 12 provides high stability of the stem 10 against rotation combined with a large area of contact with the bone cortex, which results in extremely reliable primary stability of the stem 10 within the marrow cavity of a femur (not shown). In addition, the basically rectangular shape of the shank 12 offers the additional biological advantage that the marrow cavity need not be completely reamed out before the stem is inserted, as a result of which the femur receives an adequate nutritive supply from the marrow cavity, which is a prerequisite for secondary osteointegration of the implant.

At the same time, the shank 12, which has a distal end 14 and a proximal end 16, is substantially conical in shape; the distal end 14 of the shank 12 tapering in a substantially conical manner. The distal end 14 is also somewhat rounded, with a continuous transition to a pyramidal tip. Owing to this construction, points of peak tension at the femur are avoided, which can improve both the healing process and the life expectancy of the femoral hip-joint endoprosthesis as a whole.

A medial narrow side 18 of the shank 12 has the shape of a polynomial function designed to represent the curve of the femur in the region of the calcar. In this way, the gap that is necessarily created when spongiosa bone is extensively reamed out of the calcar region can subsequently be filled by the stem 10 when it is inserted into the femur. An associated advantage is that the proximal force transmission is considerably improved.

In the region of the proximal end 16, the medial narrow side 18 of the shank 12 is continuous with a neck 20. The neck 20, which is reinforced in the region of the transition from the shank 12 to the proximal end 16 in order to avoid the risk of fracture, becomes narrower toward its junction with a frusto-conical-member 22 that is provided to receive a joint ball (not shown). Such tapering of the neck 20 increases the mobility in the artificial hip joint by as much as 3°.

A lateral narrow surface 24 of the shank 12, which is slightly concave, is continuous with a trochanter wing 26 in the region of the proximal end 16 of the shank 12. The trochanter wing 26 stabilizes the stem 10 by enlarging the proximal anchoring surface in the femur. In addition, the trochanter wing 26 is extremely important in relation to compression of the bone in the final phase of insertion of the proximal end 16 of the shank 12. For example, during the surgical manipulations the trochanter wing 26 can prevent the shaft 12 from sinking in too far in problematic cases.

The trochanter wing 26 itself is penetrated by a row of bores 28 or the like, which both serve to assist observation of the bone material or its structure and identification of the stem 10 in X-ray images, and to provide extra anchoring by the gradual ingrowth of femoral bone material. Finally, the lateral narrow surface 24 has beveled edges 30 or the like in the region of the trochanter wing 26.

The proximal end 16 of the shank 12 of the stem 10 illustrated in FIGS. 1 to 6 further includes an insertion means in the form of a shaped insertion wall unit 32 for use in the insertion of the stem 10 into the marrow cavity of the femur. The position of the insertion wall unit 32 at the proximal end 16 of the shaft 12 is substantially on the median long axis 34 of the stem 10 so that force is transmitted coaxially. The insertion means 32 comprises an abutment surface 36 for an insertion tool (not shown), oriented approximately transversely with respect to the median long axis 34 of the stem 10.

The abutment surface 36 is of substantially V-shaped cross section pointing toward the distal end 14 of the shank 12. In particular, as shown in FIG. 3, the substantially V-shaped abutment surface 36 is composed of two faces 38, 40, each set at an angle $\alpha$ in the range 15° to 45° inclusive and preferably at an angle of 30° with respect to a horizontal plane 42, which is perpendicular to a median longitudinal plane 46 (cf. FIGS. 5 and 6) of the stem 10. The intersection line 44 of the two faces 38, 40 of the approximately V-shaped abutment surface 36 also coincides with the median longitudinal plane 46.

Alternatively, as shown in FIG. 3a, the abutment surface 36 can be substantially concavely recessed as at 38a toward the distal end 14 of the shank 12. In this case the anticlinal 44a line of the approximately concave abutment surface 36, like the intersection line 44, would coincide with the median longitudinal plane 46 of the stem 10.

The insertion means 32 can further be provided with a bore coaxial with the median long axis 34, to accept a pin or the like projecting from the insertion tool, in order to provide additional centering and/or fixation and/or positioning of the insertion tool during insertion of the stem 10.

The proximal end 16 of the shaft 12 further comprises an extraction means 47 for removing the stem 10 from the marrow cavity of the femur. The extraction means 47, like the insertion means 32, is positioned at the proximal end 16 of the shaft 12 substantially on the median long axis 34 of the stem 10 so that force is transmitted coaxially. The extraction means 47 comprises a bore 48 with a screw thread 50 for an extraction tool (not shown), the median long axis of the bore 48 coinciding with the median long axis 34 of the stem 10.

In the first exemplary embodiment of the stem 10 shown in FIGS. 1 to 6, the bore component of the insertion means to receive a pin or the like projecting from the insertion tool is identical with the bore 48 with the screw thread 50 for the extraction tool that is a component of the extraction means 47. To prevent the thread 50 from being damaged when the stem 10 is impacted into the marrow space of the femur, the first turn of the thread 50 is set slightly back within the bore 48.

Turning now to the second embodiment of stem 10 shown in FIG. 7, there is extensive correspondence with the first embodiment shown in FIGS. 1 to 6, and identical parts are indicated by the same reference numbers.

The second embodiment shown in FIG. 7 differs from the first embodiment only by the presence of two longitudinal ribs 52 or the like on the lateral narrow surface 24 near the trochanter wing 26 at the proximal end 16 of the shaft 12. The two longitudinal ribs 52, oriented approximately parallel to the median long axis 34 of the stem 10, serve as an additional guide for the stem 10 during insertion into or extraction from the marrow cavity of the femur. Each of the longitudinal ribs 52 is formed by two surfaces 54, 56 enclosing an angle β of between 90° to 120° inclusive in an approximately V-shaped configuration.

To improve the biological fixation by ingrowth of femoral tissue into the implant, the stem 10 is made of metal, in particular of titanium or a titanium alloy, the surface of the shaft 12 preferably having an average surface roughness of 3 to 5 μm.

What is claimed is:

1. In a stem for a femoral hip-joint endoprosthesis the stem including a shaft of substantially rectangular cross section and defining a distal end and a proximal end, said shaft having a median long axis, said distal end tapering in a substantially conical manner and adapted to be inserted into a marrow cavity of a femur, an insertion wall unit located at the proximal end of said shaft for receiving an insertion tool for establishing a force on said proximal end for insertion of the shaft into said marrow cavity of the femur, a member to receive a joint ball, said member being located at the proximal end of the shaft, and a neck member forming a connection between said member and said proximal end of the shaft, and further including the improvement having said insertion wall unit at said proximal end of said shaft being substantially on said median long axis of said shaft to transfer force applied to said insertion wall unit to said shaft along said median long axis, said insertion wall unit including first and second laterally extended abutment faces and having a common connecting portion aligned with said axis, said abutment faces including said common connecting portion extending substantially perpendicular from and to opposite sides of said median long axis of said shaft, said faces extending outwardly from said common connecting portion and forming an outwardly extended open surface, said open surface being adapted to receive an insertion tool with the force concentrated on said open surface along said median long axis.

2. A stem as claimed in claim 1, having an extraction means located at the proximal end of the shaft for use in the extraction of the shaft from the marrow cavity of the femur, said extraction means being located substantially on said median long axis of said shaft so that force on said shaft during said extraction of the shaft is coaxial with said median long axis.

3. A stem as claimed in claim 2, wherein said extraction means defines a bore with a screw thread for cooperation with an extraction tool, said bore being positioned so that the median long axis of the bore coincides with said median long axis of the shaft.

4. A stem as claimed in claim 1, wherein said abutment faces form a substantially V-shaped abutment surface having a cross section pointing toward said distal end of the shaft.

5. A stem as claimed in claim 4, wherein each of said laterally extending abutment faces forms an angle α in the range of 15° to 45° inclusive with respect to a transverse plane perpendicular to a median longitudinal plane of the shaft.

6. A stem as claimed in claim 1, wherein said abutment faces form a substantially concave abutment surface at the proximate end and extending outwardly of the distal end of the shaft.

7. A stem as claimed in claim 6, wherein said concave abutment surface defines an anticlinal line which coincides with a median longitudinal plane of the shaft.

8. A stem as claimed in claim 2, wherein said shaft includes a bore which is coaxial with said median long axis of the shaft and which is capable of accepting a pin projecting from an insertion tool for centering and fixation of the insertion tool.

9. A stem as claimed in claim 1, wherein said shaft includes a bore which is coaxial with said median long axis of the shaft and which is capable of accepting a pin projecting from an insertion tool for centering and fixation of the tool, said bore having an inner threaded portion forming a part of an extraction means for receiving a tool including an end portion adapted to extend into said bore and having a screw thread for engaging said threaded portion, a first turn of said thread portion being set back into the bore.

10. A stem as claimed in claim 1, comprising a trochanter wing continuous with said proximal end of the shaft, said shaft including a lateral narrow surface adjacent to said trochanter wing and extending from said trochanter wing to said distal end of the shaft, the lateral narrow surface includes at least one longitudinal rib which is oriented substantially parallel to said median long axis of the shaft and guides the shaft during insertion of said shaft into the femur.

11. A stem as claimed in claim 10, wherein said longitudinal rib includes two components oriented to define a substantially V-shaped member and wherein said V-shaped member encloses an angle $\alpha$ in a range of 90° and 120° inclusive.

12. A stem as claimed in claim 1, wherein said shaft is metallic and substantially of titanium.

13. A stem as claimed in claim 1, wherein said shaft has an average surface roughness in the range of 3 to 5 µm inclusive.

* * * * *